(12) United States Patent
Sutton et al.

(10) Patent No.: US 11,244,076 B2
(45) Date of Patent: Feb. 8, 2022

(54) METHOD FOR ENABLING TRUST IN COLLABORATIVE RESEARCH

(71) Applicant: McMaster University, Hamilton (CA)

(72) Inventors: Andrew Sutton, Oakville (CA); Reza Samavi, Toronto (CA); Thomas E. Doyle, Hamilton (CA); David Koff, Ancaster (CA)

(73) Assignee: McMaster University

( * ) Notice: Subject to any disclaimer, the term of this patent is extended or adjusted under 35 U.S.C. 154(b) by 0 days.

(21) Appl. No.: 16/552,705

(22) Filed: Aug. 27, 2019

(65) Prior Publication Data

US 2020/0074118 A1    Mar. 5, 2020

Related U.S. Application Data

(60) Provisional application No. 62/724,825, filed on Aug. 30, 2018.

(51) Int. Cl.
G06F 21/64 (2013.01)
G16H 10/60 (2018.01)
G06F 16/23 (2019.01)

(52) U.S. Cl.
CPC .......... *G06F 21/64* (2013.01); *G06F 16/2358* (2019.01); *G06F 16/2379* (2019.01); *G16H 10/60* (2018.01)

(58) Field of Classification Search
CPC ............. G06F 16/2358; G06F 16/2379; G06F 21/6245; G06F 21/64; G16H 10/60; G16H 50/30
USPC .......................................................... 726/3
See application file for complete search history.

(56) References Cited

U.S. PATENT DOCUMENTS

| | | | |
|---|---|---|---|
| 2020/0034553 A1* | 1/2020 | Kenyon | H04L 9/3239 |
| 2020/0076602 A1* | 3/2020 | Redpath | H04L 9/3218 |
| 2020/0185070 A1* | 6/2020 | Dahmani | G06Q 20/10 |

OTHER PUBLICATIONS

Blockchain protocols in clinical trials: Transparency and traceability of consent (Fourth Version) Mehdi Benchoufi, Raphael Porcher, Philippe Ravaud https://f1000research.com/articles/6-66/v4 (Year: 2017).*

The Economist, "Apple and amazon's moves in health signal a coming transformation," Feb. 2018. [Online]. Available: https://www.economist.com/news/business/21736193-worlds-biggest-tech-firms-see-opportunity-health-care-which-could-mean-empowered.

M. Mercuri, M. M. Rehani, and A. J. Einstein, "Tracking patient radiation exposure: Challenges to integrating nuclear medicine with other modalities," Journal of Nuclear Cardiology, vol. 19, No. 5, pp. 895-900, 2012.

M. M. Rehani, "Challenges in radiation protection of patients for the 21st century," American Journal of Roentgenology, vol. 200, No. 4, pp. 762-764, 2013.

(Continued)

*Primary Examiner* — Benjamin A Kaplan
(74) *Attorney, Agent, or Firm* — Bereskin & Parr LLP/S.E.N.C.R.L., s.r.l.

(57) ABSTRACT

The presented application is a method for enabling verifiable trust in collaborative data sharing environments. The architecture supports the human-in-the-loop paradigm by establishing trust between participants, including human researchers and AI systems, by making all data transformations transparent and verifiable by all participants.

14 Claims, 9 Drawing Sheets

| Actor Type | Requirements |
|---|---|
| Data Contributors | 1) Provide consent regarding their data<br>2) Know who is accessing and sharing their data<br>3) Know when their data is being accessed and shared |
| Data Custodians | 1) Remain in control of the data<br>2) Securely store private data<br>3) Comply with data protection and DSA policies and obligations |
| Researchers | 1) Access patient data<br>2) Access AI System outcomes<br>3) Comply with DSA policies and obligations<br>4) Provide feedback to the AI system |
| Auditors | 1) Monitor actor compliance |
| AI Systems | 1) Comply with DSA policies and obligations<br>2) Provide analytical outcomes for researchers |

(56) References Cited

OTHER PUBLICATIONS

R. Samavi and M. P. Consens, "Publishing I2tap logs to facilitate transparency and accountability," in The 23rd International World Wide Web Conference (WWW'14) Workshop on Linked Data on the Web, 2014.

M. J. Field, B. Lo et al., "Conflict of interest in medical research, education, and practice", Institute of Medicine of the National Academies, 2009, 436 pages.

B. Schneier, "Applied Cryptography: Protocols, Algorithms, and Source Code in C.", John Wiley & Sons. 2nd Edition. Jan. 1, 1996.

P. Alexander, G. Kimmell, and D. Burke, "Security as a system property: Modeling Trust and Security in Rosetta," Jan. 4, 2007. pp. 1-24.

Symantec, 2018. [Online]. Available: https://www.symantec.com/. Accessed: Nov. 12, 2019.

MIT Kerberos, "Kerberos: The network authentication protocol," 2009. https://web.mit.edu/kerberos/. Accessed Nov. 5, 2019.

Y. Li, "The case analysis of the scandal of enron," International Journal of business and management, vol. 5, No. 10, p. 37, 2010.

C. A. Kushida, D. A. Nichols, R. Jadmicek, R. Miller, J. K. Walsh, and K. Griffin, "Strategies for de-identification and anonymization of electronic health record data for use in multicenter research studies," Medical care, pp. S82-S101, 2012.

G. S. Nelson, "Practical implications of sharing data: a primer on data privacy, anonymization, and de-identification," in SAS Global Forum Proceedings, 2015. 23 pages.

F. Zafar, A. Khan, S. Suhail, I. Ahmed, K. Hameed, H. M. Khan, F. Jabeen, and A. Anjum, "Trustworthy data: A survey, taxonomy and future trends of secure provenance schemes," Journal of Network and Computer Applications, vol. 94, pp. 50-68, 2017.

J. Freire, D. Koop, E. Santos, and C. T. Silva, "Provenance for compu- tational tasks: A survey," Computing in Science & Engineering, vol. 10, No. 3, 2008.

H. K. Patil and R. Seshadri, "Big data security and privacy issues in healthcare," Big Data (BigData Congress), 2014 IEEE International Congress on. IEEE, 2014, pp. 762-765.

K. Veeramachaneni, I. Arnaldo, A. Cuesta-Infante, V. Korrapati, C. sBassias, and K. Li, "Ai2: Training a big data machine to defend," in IEEE International Conference on Intelligent Data and Security (IDS'16), Apr. 2016, pp. 49-54.

HL7 International, "Fhir," 2017, accessed Jun. 2017. [Online]. Available: https://www.hl7.org/fhir/index.html.

T. Heath and C. Bizer, "Linked data: Evolving the web into a global data space," Synthesis lectures on the semantic web: theory and technology, vol. 1, No. 1, pp. 1-136, 2011.

J. J. Carroll, C. Bizer, P. Hayes, and P. Stickler, "Named graphs, prove- nance and trust," in Proceedings of the 14th international conference on World Wide Web. ACM, 2005, pp. 613-622.

R. Samavi and M. P. Consens, "Publishing privacy logs to facilitate transparency and accountability," in The Journal of Web Semantics, 2018.

A. Sutton and R. Samavi, "Blockchain enabled privacy audit logs," in Proceedings of the 16th International Semantic Web Conference. Springer, 2017, pp. 1-16.

A. Sambra, H. Story, and T. Berners-Lee, "Webid 1.0: Web identity and discovery," Mar. 2014. Available: https://www.w3.org/2005/lncubator/webid/spec/identity/. Accessed: Nov. 7, 2019.

M. Mettler, "Blockchain technology in healthcare: The revolution starts here," in IEEE 18th International Conference on e-Health Networking, Applications and Services (Healthcom'16), Sep. 2016, pp. 1-3. Abstract.

A. Azaria, A. Ekbiaw, T. Vieira, and A. Lippman, "Medrec: Using blockchain for medical data access and permission management," In 2nd International Conference on Open and Big Data (OBD'16), Aug. 2016, pp. 25-30.

X. Yue, H. Wang, D. Jin, M. Li, and W. Jiang, "Healthcare data gateways: Found healthcare intelligence on blockchain with novel privacy risk control," Journal of Medical Systems, vol. 40, No. 10, p. 218, 2016. Abstract.

K. Peterson, R. Deeduvanu, P. Kanjamala, and K. Boles, "A blockchain-based approach to health information exchange networks," 2016. 10 pages.

M. Pilkington, "Blockchain technology: principles and applications," Research Handbook on Digital Transformations, 2015. 39 pages.

S. Nakamoto, "Bitcoin: A peer-to-peer electronic cash system," http://www.bitcoin.org. Accessed: Nov. 7, 2019. 2008.

S. Melnik, "Rdf api draft: Cryptographic digests of rdf models and statements," 2001. Https://www- db.stanford.edu/~melnik/rdf/api.htmi#diges. Accessed: Nov. 7, 2019.

J. J. Carroll, "Signing rdf graphs," in International Semantic Web Conference. Springer, 2003, pp. 369-384.

C. Sayers and A. H. Karp, "Computing the digest of an rdf graph," Mobile and Media Systems Laboratory, HP Laboratories, Palo Alto, USA, Tech. Rep. HPL-2003-235, vol. 1, 2004.

J.A. Fisteus, N.F. Garc'ia, L.S. Ferna'ndez, andC.D.Kloos, "Hashing and canonicalizing notation 3 graphs," Journal of Computer and System Sciences, vol. 76, No. 7, pp. 663-685, 2010.

A. Sutton and R. Samavi, "Timestamp-based integrity proofs for linked data," Proceedings of the international Workshop on Semantic Big Data. ACM, 2018, p. 4.

C. Castelluccia, P. Druschel, S. Hu'bner, A. Pasic, B. Preneel, and H. Tschofenig, "Privacy, accountability and trust—challenges and opportunities," ENISA. Http://www. enisa. europa. eu/activities/identity-and-trust/library/deliverables/pat-study/at download/fullReport, 2011.

HL7 International, "Fhir security," 2017, accessed Apr. 2018. Https://www.hl7.org/fhir/security.html.

D. Bradbury, "The problem with bitcoin," Computer Fraud & Security, vol. 2013, No. 11, pp. 5-8, 2013.

Microsoft, "The stride threat model," 2005. Https://msdn.microsoft.com/en- us/librarylee823878(v=cs.20).aspx.

OpenLink Software, "Virtuoso universal server," 2017. Https://virtuoso.openlinksw.com/.

The Linux Foundation, "Hyperledger fabric documentation," 2018, accessed Jun. 2017. Available: https://hyperledger-fabric.readthedocs.io/en/release- 1.1/.

"Hyperledger explorer," 2018. Https: //www.hyperledger.org/projects/explorer. Accessed: Nov. 12, 2019.

L. A. Linn and M. B. Koo, "Blockchain for health data and its potential use in health it and health care related research," 2017.

C. McFarlane, M. Beer, J. Brown, and N. Prendergast, "Patientory: A healthcare peer-to-peer emr storage network v1. 0," 2017.

J. Sotos and D. Houlding, "Blockchains for data sharing in clinical research: Trust in a trustless world," 2017.

X. Liang, J. Zhao, S. Shetty, J. Liu, and D. Li, "Integrating blockchain for data sharing and collaboration in mobile healthcare applications," in Personal, Indoor, and Mobile Radio Communications (PIMRC), 2017 IEEE 28th Annual International Symposium on. IEEE, 2017, pp. 1-5.

G. Zyskind, O. Nathan, and A. Pentiand, "Decentralizing privacy: Using blockchain to protect personal data," in 2015 IEEE Security and Privacy Workshops, May 2015, pp. 180-184.

L. Xu, L. Chen, N. Shah, Z. Gao, Y. Lu, and W. Shi, "Dl-bac: Distributed ledger based access control for web applications," in Proceedings of the 26th International Conference on World Wide Web Companion. International World Wide Web Conferences Steering Committee, 2017, pp. 1445-1450.

M. Suleyman and B. Laurie, "Trust, confidence and verifiable data audit," Mar. 2017. Https://deepmind.com/blog/trust- confidence-verifiable- data- audit/.

Google, "Trillian: A Transparent, Highly Scalable and Cryptographically Verifiable Data Store," Https://github.com/google/trillian, 2018. Accessed: Nov. 12, 2019.

A. Eijdenberg, B. Laurie, and A. Cutter, "Verifiable data structures," Nov. 2015. Https://www.continusec.com/static/VerifiableDataStructures. Accessed: Nov. 12, 2019.

\* cited by examiner

| Actor Type | Requirements |
|---|---|
| Data Contributors | 1) Provide consent regarding their data<br>2) Know who is accessing and sharing their data<br>3) Know when their data is being accessed and shared |
| Data Custodians | 1) Remain in control of the data<br>2) Securely store private data<br>3) Comply with data protection and DSA policies and obligations |
| Researchers | 1) Access patient data<br>2) Access AI System outcomes<br>3) Comply with DSA policies and obligations<br>4) Provide feedback to the AI system |
| Auditors | 1) Monitor actor compliance |
| AI Systems | 1) Comply with DSA policies and obligations<br>2) Provide analytical outcomes for researchers |

```
1  _:data-sharing-graph {
2  _:data-sharing-graph a https://example.com/
       DataSharingTransaction ;
3  _:hasTxType "pointer"^^xsd:string ;
4  _:hasTimestamp "1517263159399"^^xsd:string ;
5  _:hasSender "University_Medical_Center"^^xsd:string ;
6  _:hasReceiver "Example_Hospital"^^xsd:string ;
7  _:hasPrivacyEvent _:privacy-graph-header ;
8  _:hasFHIRURL http://fhir.example.com/DiagnosticReport?
       id=system%7C00003. }
```

FIG. 6

```
1  @prefix l2tap:<http://purl.org/l2tap#> .
2  @prefix scip:<http://purl.org/scip#> .
3  @prefix xsd: <http://www.w3.org/2001/XMLSchema#> .
4  _:privacy-graph-header {
5    _:logevents-e4 a l2tap:PrivacyEvent ;
6    l2tap:eventParticipant _:participants-hc1 ;
7    l2tap:receivingTimestamp "2018-01-29T12:00:00Z"^^xsd:
         dateTime ;
8    ... }
9  _:privacy-graph-body {
10   _:requests-req1 a scip:AccessRequest ;
11   scip:dataRequestor _:researcher-2 ;
12   scip:dataSender _:researcher-1 ;
13   scip:dataSubject _:patient-1234 ;
14   scip:requestedDataItem _:patient-1234-CTScan ;
15   scip:requestedPurpose _:purposes-treatment ;
16   ... }
```

FIG. 7

```
1  @prefix sig: <http://icp.it-risk.iwvi.uni-koblenz.de/
       ontologies/signature.owl#> .
2  _:sig-graph {
3    # graph signing methods omitted
4    _:sig-graph a sig:Signature ;
5      sig:hasVerificationCertificate <signer_webid> ;
6      sig:hasSignatureValue "BC3A14C44DEBF82A..."^^xsd:
           string ;
7      l2tap:hasSignedGraph _:privacy-graph-header, _:data-
           sharing-graph . }
```

METHOD FOR ENABLING TRUST IN COLLABORATIVE RESEARCH

METHOD FOR ENABLING TRUST IN COLLABORATIVE RESEARCH

This application claims the benefit of U.S. Provisional Application Ser. No. 62/724,825, filed Aug. 30, 2018, which is hereby incorporated herein by reference.

FIELD

The present application relates to a method enabling verifiable trust in collaborative data-sharing environments.

BACKGROUND

The era of immense data analytics is transforming health care with the ability to interpret large and diverse datasets to provide better diagnoses, manage complex diseases, improve efficiency of care, and generate aggregated data for Artificial Intelligence (AI) systems [1]. For instance, Alphabet, the parent company of Google, has launched a new initiative called Cityblock Health that will provide low income households with medical care by analyzing multiple datasets to determine where care is needed [1]. Furthermore, IBM Watson's cognitive computing platform uses multiple large datasets to generate predictive analytics for improved diagnoses. In both examples, individuals (or patients) are actively and continuously involved in contributing data to be fed to the AI systems and the research goal is achieved through an intense (sometimes real time) collaboration between humans (as the data contributors), diverse researchers from multiple disciplines (e.g., medicine, computer science, statistics) and AI systems. The active involvement of humans (or patients) in this type of emerging health research is different to their roles in the classical clinical trial type research where a limited number of patients are involved and the patient's connection to the research ends when the data collection step is over. For data analytics health research, a feedback loop among patients, researchers and AI systems needs to be maintained in order to improve the predictive model. However, a successful realization of such a human-in-the-loop paradigm for health research requires establishing verifiable trust among participants (including humans and AI systems). The following motivating scenario reveals the challenges in maintaining trust among participants.

Figure 1:
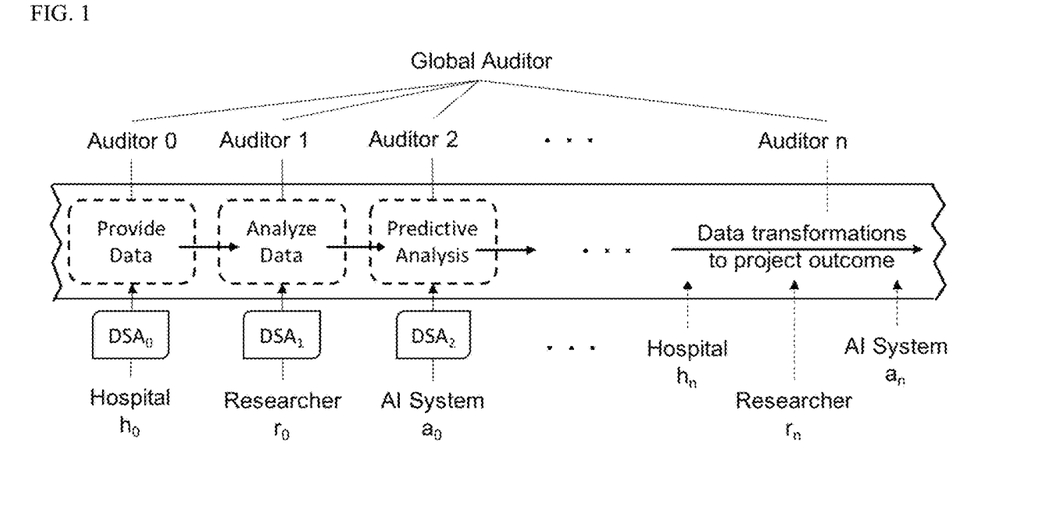
FIG. 1 shows the collaborative research pipeline.

As part of a multi-disciplinary research team, the inventors are currently developing an active classifier to predict a patients' specific health. The classifier is active since the machine learning model will be constantly refined as individuals contribute their data points. Then the next patient at the point of care will benefit from the updated risk assessment model while she has a chance to contribute her data for the consequent model refinement iteration. Such a complex collaboration on private data requires multiple Data Sharing Agreements (DSA) to be devised between diverse groups of researchers and hospitals as each participant may adhere to different privacy policies and jurisdictions. In addition, patients are in the loop of research since the AI system needs to be updated in near real time to produce accurate and relevant cancer risk assessment for each patient [2], [3]. FIG. 1 conceptualizes the collaborative research pipeline for such a scenario, where hospitals h0, hn provide data for participants and multiple researchers r0, rn and AI systems a0, . . . , an provide data analytics on the datasets. Hospitals continuously provide data as it is generated, and DSA0, . . . , DSAn govern access to the datasets in the research pipeline. Auditing the data lifecycle (from collection to use, disclosure and transformation) is essential in this scenario to ensure accountability. Typically, local and global auditors oversee the process [4], and the trust between different auditors and researchers is a presumption, however in reality there are conflicts of interests that may undermine the presumed trust [5].

A trusted system means that all parties accept the actions of the system to be correct, the system's outputs to be true, and that the system will complete its expected task [6]. The trustworthiness of a system depends on the level of perceived trust of each system component [7]. Typically, trust is a subjective measurement based on the perception of how different parties evaluate each other and the systems they interact with. Achieving a trustworthy system requires transforming the notion of trust into an objective measurement. This transformation often relies on the use of a centralized trusted third party, where all collaborating parties trust this external entity (e.g., certificate authorities in public key infrastructures [8], arbitrated protocols [9]). Establishing trust through a centralized third party is often the source of collusion, which threatens the trust, the very central notion that collaborative parties intend to establish. The Enron Scandal [10] is a textbook case when the trust placed in the centralized auditors was a major factor in the fraud. Rather than a centralized approach, we can leverage a distributed system to support trust between collaborating parties and alleviate the disadvantages that tend to threaten trust in centralized systems.

SUMMARY

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

In this paper, we propose a distributed approach through a blockchain-based architecture to digitize trust in collaborative health research environments where actors who do not necessarily trust each other can effectively collaborate to achieve a research goal. By using a permissioned blockchain (a blockchain that is controlled by authenticated participants as opposed to a public blockchain used for crypto-currencies) we support a collaborative environment that all data activities are transparent and can be verified by all participants. To protect data subjects' privacy and manage the data size, we define a concept of data sharing transactions where data is made accessible through data pointers that rely on institutional-based access control, data pointers are stored on the blockchain, and privacy policies related to each data item are captured. Transactions stored on the blockchain provide a tamper-proof trail of data while integrity verification can be performed and participants cannot repudiate their actions.

Current approaches on protecting individuals' privacy and maintaining trust in collaborative research are based on data anonymization [11], [12] and provenance management, i.e., tracking the collection, use, disclosure, and transformation of data items throughout the research pipeline [13], [14]. These approaches are necessary, but insufficient when trust is not guaranteed between collaborators, especially when AI systems are also considered as participants in the process of data transformation. Provenance and data anonymization methods can be supplemented by digitizing trust to mitigate the risk of collusion between auditors and researchers or inadvertent breaches of data usage by AI systems.

DRAWINGS

The embodiments of the application will now be described in greater detail with reference to the attached drawings in which.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

II. Architecture

A common approach for maintaining trust in collaborative environments relies on a centralized party to oversee researchers' activities. Centralized systems are generally sources of data breaches and more importantly, collusion between actors is difficult to prevent or detect. With the emergence of blockchain technology, the issues involved with a centralized trust system are alleviated through the use of distributed trust where all interactions are distributed, immutable, transparent and consensually agreed upon. Adapting blockchain from the typical crypto-currency use case to collaborative health research requires overcoming multiple challenges. First, transactions in health research involve immense data sizes (e.g., an entire health record with all medical imaging history [15]). Second, specific privacy statements must be captured for each individual data item, which might be applicable for all transactions. Therefore, blockchain adaptation for health research transactions requires careful investigation of the relationship between data and what is stored on the blockchain and the privacy of data subjects.

In this section we identify the classes of participants and their requirements when collaborating in a research environment as well as the properties required for a system to be trustworthy (Section II-A). We then describe an architecture that supports blockchain enabled self-governed trust (Section II-B), where specific components are detailed in Sections II-C, II-D, and II-E, respectively.

A. Desiderata

Figure 2:
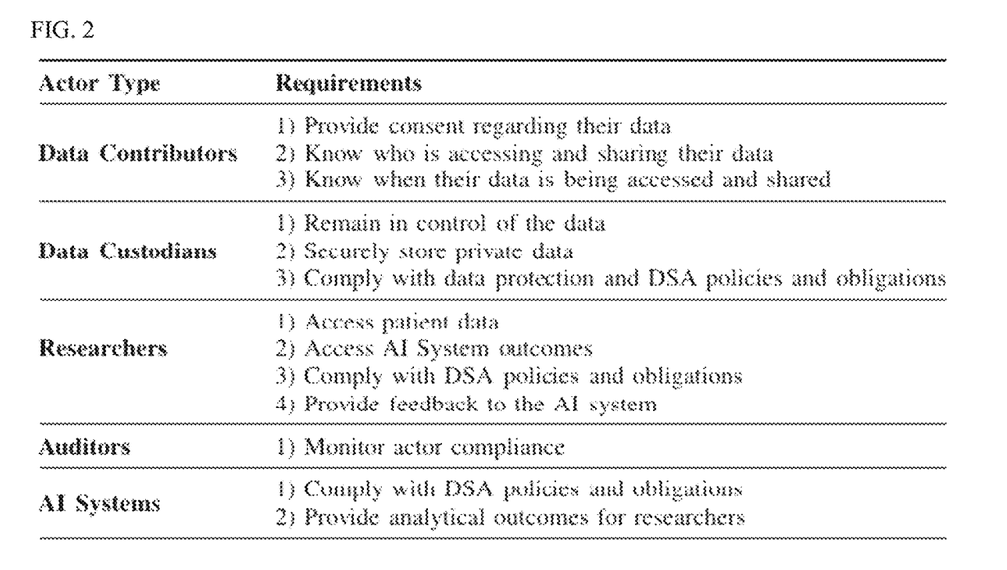
FIG. 2 shows the system actors and requirements

Actors involved in collaborative health research include the data contributors (e.g., patients), data custodians (e.g., hospitals and research institutes), AI systems (e.g., active machine learning system [16]), researchers, and auditors. Patients are the source of the contributed data (e.g., subject of a CT scan) while data custodians store this data in their information systems. In an environment that involves the interaction of private health data among multiple actors, the data contributors want to know who is accessing and sharing their data, as well as when and what through some consent mechanisms. Data custodians are responsible for securely storing private health data while researchers require access to this data to perform analysis. Furthermore, AI systems also need to access patient data to update their predictive models. Finally, auditors monitor the system actors to determine compliance to privacy policies stated in DSAs and consent directives. The details of each actor type and their specific requirements are summarized in FIG. 2.

For an architecture to be trustworthy, certain properties need to be present. Security properties that support trustworthy systems are grouped into six domains: confidentiality, integrity, availability, authentication (access control), non-repudiation, and accountability (transparency) [7]. Confidentiality and integrity define mechanisms that prevent the unauthorized reading and writing of data, respectively. Mechanisms such as encryption, digital signatures, and cryptographic hash functions support these properties. Ensuring that resources are accessible when required by authorized users falls under the availability category. Our proposed architecture relies on external mechanisms to support the availability of the system and is therefore considered out of scope for this research. Authentication and access control provide processes for verifying the identity of an entity and maintaining the entity's privilege across the system, respectively. The use of digital signatures and cryptographic hash functions support non-repudiation by creating undeniable evidence that an action has occurred. Finally, accountability and transparency, an extension of non-repudiation, capture non-compliant users and support the maintenance of user privacy through the use of logging and auditing. An ideal trustworthy system aims to support all six domains and properties to establish digitized trust. Especially in a health research environment that deals with private patient data, our proposed architecture must support these trust properties to provide a trustworthy system.

B. Architectural Overview

Figure 3:
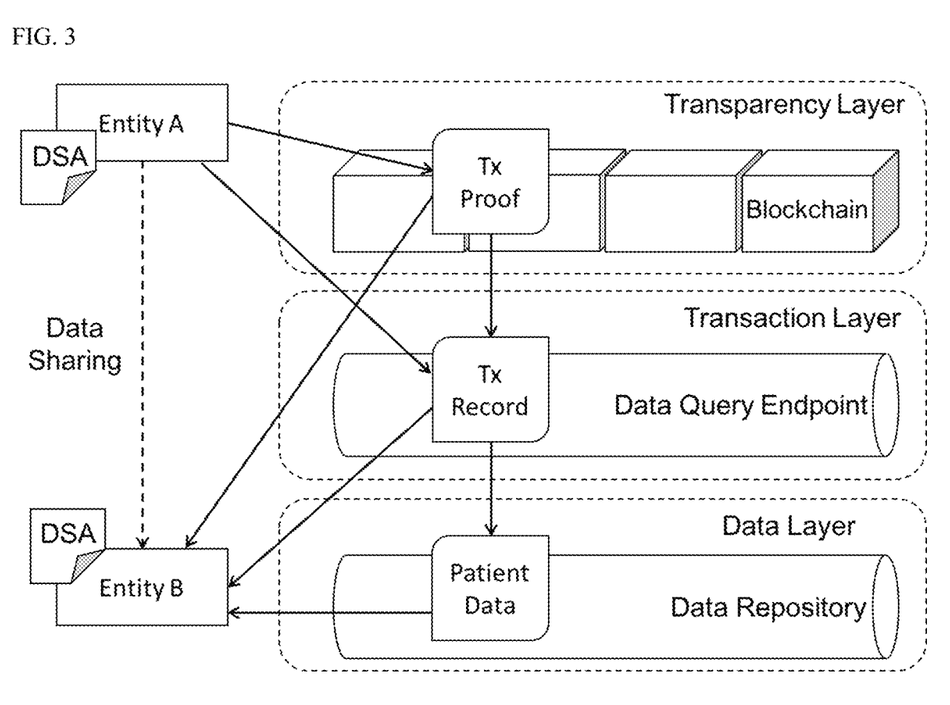
FIG. 3 shows the architecture layers

Given the requirements of each class of actors (FIG. 2) and the trustworthy system requirements, our architecture should support three main functionalities: provenance management of research data, privacy management of data subjects, and distributed and verifiable trust among participants. We present a layered architectural approach, as shown in FIG. 3, with three layers to support data transactions, privacy and trust. At the bottom is the data layer responsible for generating data pointers that link to the medical records and can be shared among actors. Data pointers allow for the data custodians to remain in operational control of the data and provide their institutional-based access control mechanisms to protect the data. The middle layer is the transaction layer responsible for providing a mechanism for storing and querying data sharing transactions, including provenance and privacy information. At the top is the transparency layer responsible for distributed trust between all participants by allowing all data transactions to be transparent among all participants. A layered approach has multiple advantages. The functionality and the applied technology can be decoupled so that connections between components are clearly defined and a component does not rely on the internal logic and the technology used in other components. For example, a permissioned blockchain can be used as a plug-in for the transparency layer without changing any blockchain properties. The relationships between layers and how the layers work together are describe below. The internal specifications of each layer are described in subsequent subsections.

Figure 4:
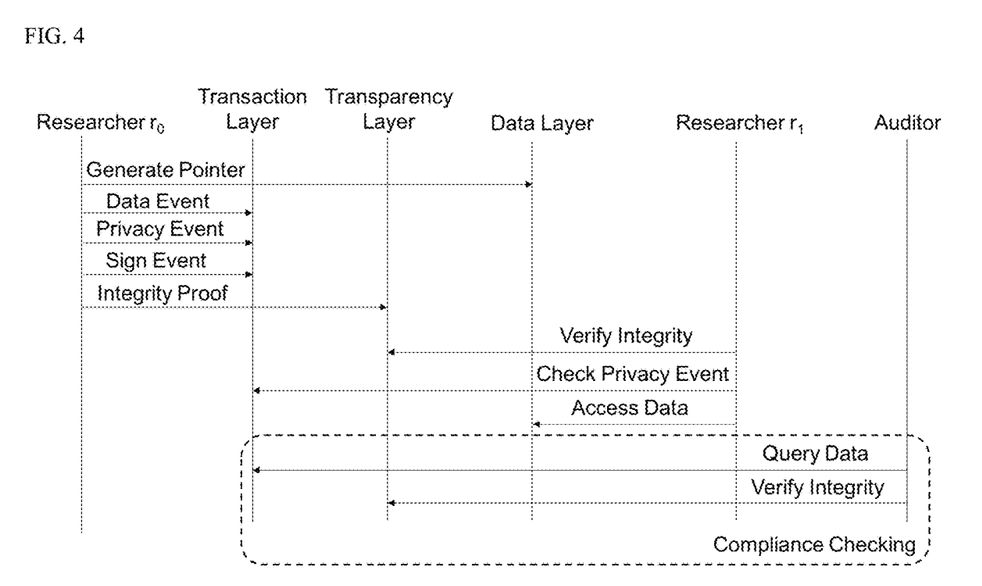
FIG. 4 shows the data sharing transaction sequence

The collaborative research pipeline involves multiple actors interacting with each other and sharing private health data. The sequence diagram in FIG. 4 depicts a dynamic view of the architecture in FIG. 3 and demonstrates an instance of the research pipeline where data is being shared between two researchers (r0 and r1). DSAs are established between the researchers that outline the privacy policies that the researchers must abide by when using the data. When performing a data sharing transaction, the sending entity (r0) first interacts with the data layer to generate a pointer to the data that she wants to share. The data accessible by the pointer is stored in the data layer's data repository, which is hosted at a hospital or research institute. After researcher r0 has generated the data pointer in the data layer, she constructs a data sharing transaction, which is composed of a data sharing event, privacy event, and signing event. These events provide the transaction metadata (including the pointer generated in the data layer), privacy policies related to the data, and a digital signature of the transaction. The data sharing transaction is stored in a data query endpoint so that other actors can query the transactional data. An integrity proof (i.e., cryptographic hash) of the data sharing transaction is computed and written to the transparency layer so that all participants are aware of the transaction.

After the data sharing transaction has been completed by researcher r0, researcher r1 must first query the transparency layer to verify the integrity of the transaction. Integrity verification consists of recomputing the integrity proof of the data sharing transaction and comparing it to the integrity proof in the transparency layer. If both integrity proofs match, researcher r1 can proceed to accessing the data through the data pointer specified in the data sharing transaction. Alternatively, if the integrity proof verification fails, researcher r1 should not access the data and an auditor can perform further investigation. Researcher r1 then queries the transaction layer to determine the privacy policies they must abide by when using the data and then accesses the data through the data pointer at the data layer. Finally, auditors query the transaction and transparency layers to check the compliance of all participants with the policies in the governing DSAs.

C. Data Layer

The data layer acts as a data repository where the data pointers that are shared among actors reference the actual data records. We leverage the emerging Fast Healthcare Interoperability Resources (FHIR) standard to serve as our data pointers. A set of modular components called Resources are at the core of the FHIR framework [17]. Resources represent healthcare concepts, such as patients, providers, medications, and diagnostics. Each resource has a unique URL (uniform resource locator) and can be retrieved and manipulated through these URLs. In our architecture, authorized actors access the data using the FHIR URLs. By using FHIR we can not only support local hospital access control mechanisms but we also only maintain the pointers to data (or their hash values) in other layers instead of the actual data.

D. Transaction Layer

Figure 5:
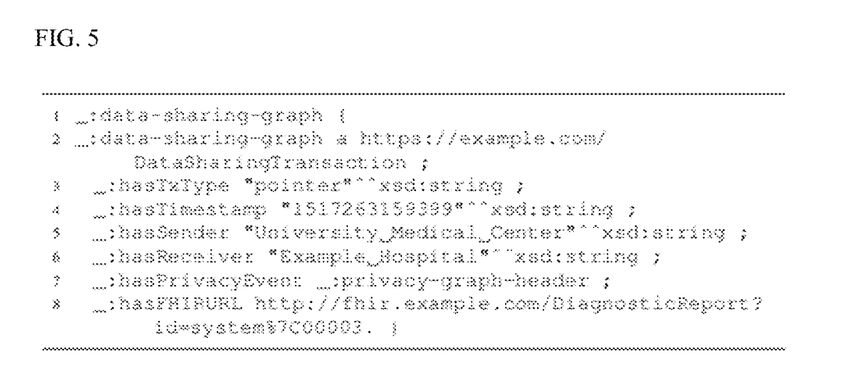
FIG. 5 shows a data sharing event graph

After the sending entity has generated the data pointer in the data layer, a data sharing transaction is generated by the transaction layer. This transaction is composed of a data sharing event, privacy event, and signing event as shown in FIG. 4. We leverage a graph data model to represent the data sharing transaction events as it provides generalizability and flexibility [18], but our approach is data model agnostic and any other data models (e.g., relational data models) can also be used. We define Linked Data named graphs [19] for each type of event. The graphs are stored in an externally accessible data query endpoint, such as a quad store or SPARQL endpoint, so that they can be queried by other authorized actors in the system. FIG. 5 represents the data sharing transaction and records the metadata of the transaction, including the sender, receiver, and timestamp (lines 4-7), the data pointer (FHIR URL) that is going to be shared (line 8), and the related privacy event graph (line 7). The transaction layer supports two types of transactions, depending on the purpose and initiator of the transaction (line 3). $T_{pointer}$ transactions specify that the transaction is sharing data pointers referencing patient data and are performed by the actors that store, generate, or manage the actual data (i.e., researchers, data custodians). The $T_{pointer}$ transactions can be queried by AI systems and by following the data pointer, the referenced data can be retrieved to update the AI system's predictive algorithm. $T_{outcome}$ transactions are performed by AI systems and specify that the transaction is sharing the results computed by their algorithms. The differentiation between $T_{pointer}$ and $T_{outcome}$ transactions allows actors to track transactions relating to data sharing and AI system predictive outcomes over the course of the research pipeline, as well as provide feedback for the AI system improvement.

Figure 6:
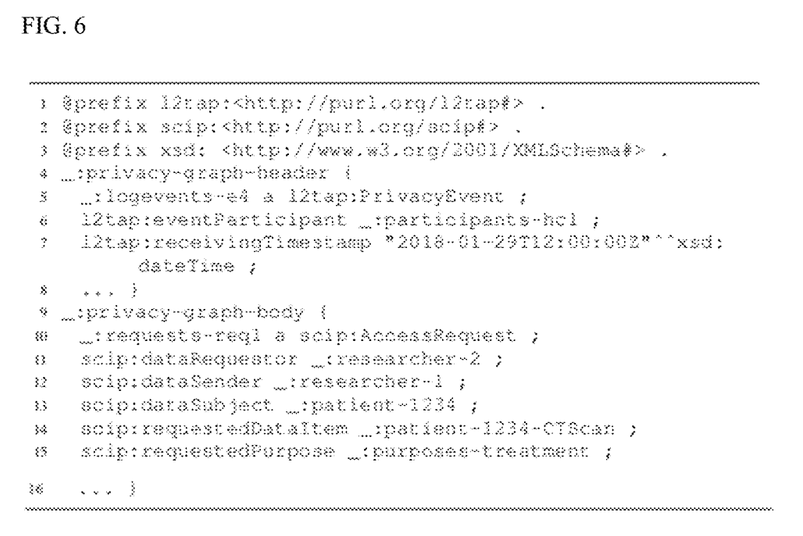
FIG. 6 shows a privacy event graph

To support accountability and transparency, a privacy event captures promised and performed privacy acts, such as expressing privacy policies, requesting access, and defining data usage and obligations. For example, the Linked Data Log to Accountability, Transparency, and Privacy (L2TAP) framework [20] can be used to generate Linked Data privacy events. FIG. 6 is an example of an L2TAP privacy event, which consists of a header that asserts provenance semantics (lines 4-8), and a body that asserts privacy semantics (lines 9-16). This privacy event is an example of an access request (line 10) that contains properties for specifying the requested data item(s) (line 14), the purpose of access (line 15), and the data sender and requester (lines 12 and 11, respectively). L2TAP privacy events can also provide assertions of requested privacy privileges (omitted); more details can be found in [20], [21].

Figure 7:
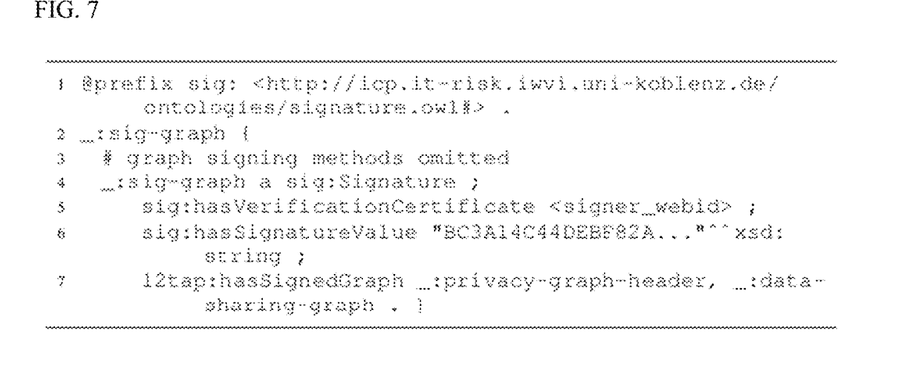
FIG. 7 shows a signature event graph

A signature event graph (FIG. 7) is used for integrity verification and provides participant non-repudiation so that data sharing actions cannot be denied. A data sender's digital signature of a data sharing and privacy event graph is captured in the signature event (line 6). The signer's public key used to verify the signature can be obtained through the signer's WebID [22] in line 5. The signed data sharing and privacy event graphs are referenced in line 7. Information describing how to verify the signature is also asserted in the graph, such as signing algorithms used (omitted). The specific algorithm for computing digital signatures for graphs is described further in [21].

E. Transparency Layer

The underlying technology used at the transparency layer is a blockchain. Blockchain technology is a suitable candidate to operate at the transparency layer by providing mechanisms to record tamper-proof data transactions among multiple untrusted actors through its distributed consensus network [23], [24], [25], [26]. A blockchain is a decentralized database composed of a continuously increasing amount of records, or blocks, that represents an immutable digital ledger of transactions [27]. Distributed ledgers allow for a shared method of record keeping where each participant has a copy of the ledger, meaning that a majority of participants (i.e., nodes on the network) will have to be in collusion to modify the records in the blockchain. Each record, or block, in the blockchain is comprised of a header containing a cryptographic hash of the previous block (forming a chain of blocks) and a payload of transactions. Blockchain is the technology behind the popular Bitcoin cryptocurrency [28], where the blockchain provides a secure and consensus-driven record of monetary transactions between participants on the network. Similar to how Bitcoin leverages blockchain, our architecture leverages a blockchain to provide transparent and tamper-proof data sharing transactions. However, unlike the popular use of blockchain for crypto-currencies (e.g. Bitcoin [28]), which is public in nature, our blockchain network is private, or permissioned, since we are dealing with personal health information and the network participants are known (i.e., the network is composed of the actors in the collaborative research environment). Since the network is permissioned, we forgo the computationally expensive cryptographic consensus protocol used in public blockchain networks, and leverage participant signature-driven consensus protocols instead.

A data sharing transaction that is generated in the transaction layer is hashed using a cryptographic hash function to generate an integrity proof of the data sharing transaction (i.e., data sharing event, privacy event, signing event graphs). There are numerous methods for computing a digest of Linked Data graphs (e.g., [29], [30], [31], [32]) and a comparative analysis of integrity proof methods was performed in [33]. We use the incremental cryptography approach in [31] since it provides an efficient runtime. Incremental cryptography produces an integrity proof of Linked Data graphs by hashing each statement in the graphs and using a commutative operation (e.g., multiplication) modulo a large prime number to merge the statement hashes into an integrity proof Formally, integrityProof=$\Pi_{r=0}^{n} h(\delta_i) \mod(p)$ where n is the number of statements in the graphs, h is a cryptographic hash function (e.g., SHA-256), si is a graph statement, and p is a large prime number.

The data sharing transaction integrity proof is stored on the blockchain to have an immutable record of the transaction and for actors to be aware of the transaction. To store the integrity proof on the blockchain, we must define a specific transaction for the network. A transaction in the transparency layer involves generating and storing a tuple t=(integrityProof, sender, receiver, txType) on the blockchain. The tuple serves as a tamper-proof record of the data sharing transaction and is composed of an integrity proof of the data sharing transaction, the sender and receiver of the transaction (e.g., researcher, AI system), and the transaction type (i.e., $T_{pointer}$ or $T_{outcome}$).

The transparency layer supports human-in-the-loop functionality, even for patients as the data contributors in the collaborative health research environment. Inherent to blockchain technology, all participants in the network contribute and maintain the ledger of transactions. Therefore, all participants can audit data sharing transactions by verifying the integrity proofs on the blockchain and querying privacy events in the transaction layer to determine compliance and adherence to DSA policies and consent directives. We also leverage smart contracts (programs that run on a blockchain network and all participants can interact with) to encode and enforce DSA constraints that are part of contractual obligations.

Examples

Figure 8:
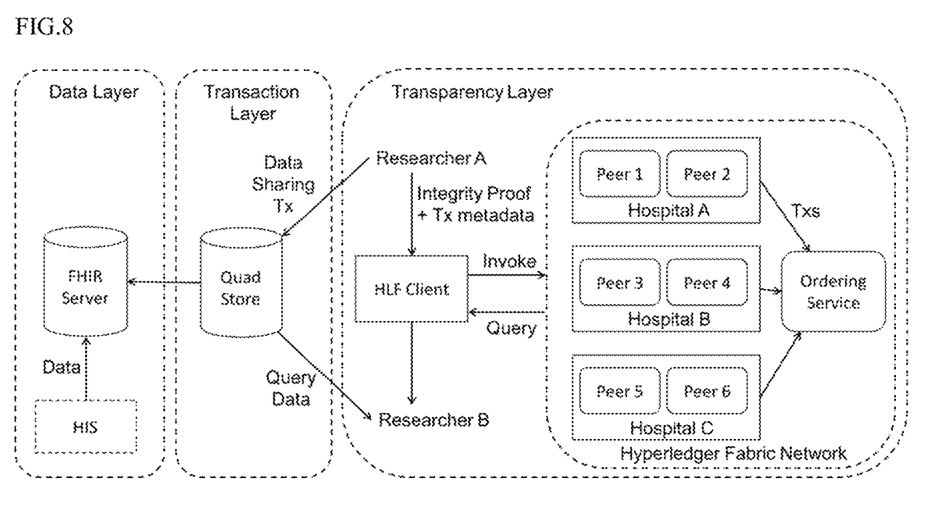
FIG. 8 shows an architecture realization

In one embodiment, We map our proposed architecture in FIG. 3 to existing and emerging technologies to demonstrate the feasibility of such a system in a realistic collaborative health research environment. The technological realization is depicted in FIG. 8. The data layer is mapped to a FHIR server from hospital information systems (HIS) that provide the data pointer services. A quad store with a SPARQL query endpoint (Virtuoso Universal Server [38]) is used for the transaction layer where the data transaction graphs are stored (and accessible through SPARQL queries). The transparency layer requires a permissioned blockchain network, so we utilized the Hyperledger Fabric blockchain platform [39].

We simulated a collaborative health research environment by running multiple virtual machines (VM), representing different actors, on a high performance cloud. Each VM is an Ubuntu 16.04 instance with 1 VCPU and 4 GB of memory. In particular, our Hyperledger Fabric blockchain network (v1.0.6) is composed of three organizations (representing research institutes or hospitals) with each organization running two peers, as shown in FIG. 8. The Fabric network also has a dedicated VM running as the network orderer and is attached to a Kafka-Zookeeper ordering service (for providing efficient transaction and block ordering). Hyperledger Fabric is capable of running smart contracts, or chaincode, and we created a DSA chaincode that enforces simple DSA constraints. Specifically, we encoded data retention periods found in DSAs and the chaincode rejects transactions that fall outside of some date range asserted by the DSA. Hyperledger Fabric stores data in the blockchain as key-value pairs, so in the case of our tuple defined in Section II-E, we map the integrity proof as the key and the remaining tuple elements as the value (represented as a JSON object). To realize the human-in-the-loop concept, we used a blockchain visualization dashboard (Hyperledger Explorer [40]) to invoke transactions and perform transaction and block-level queries.

Figure 9:
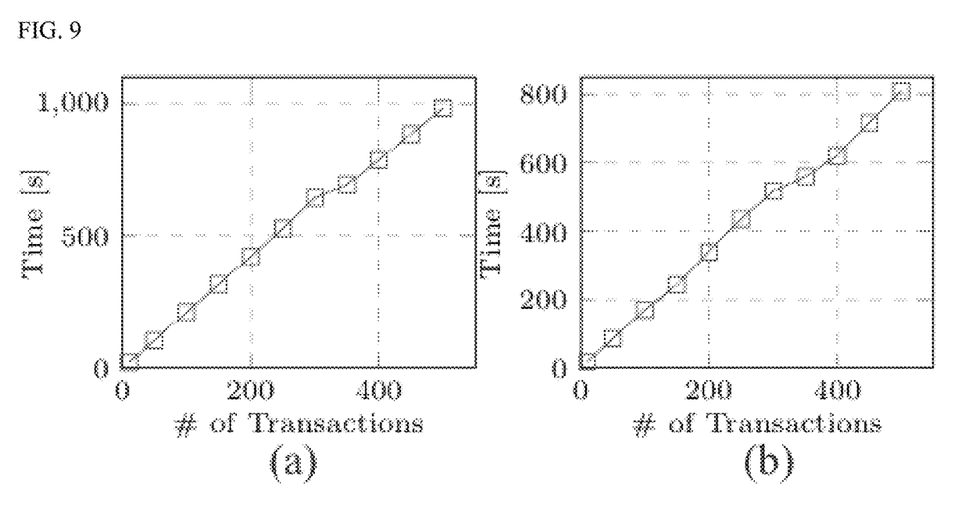
FIG. 9 shows elapsed execution times for a) data sharing transaction generation and b) integrity verification

We performed two experiments to measure the scalability of the architecture as the number of transactions increases in the research environment using the architecture realization in FIG. 8. The first experiment is from the perspective of actors that want to generate data sharing transactions and involves generating a data sharing transaction event (composed of the graphs in Section II-D), storing it in the transaction layer, computing an integrity proof of the event (using incremental cryptography) and writing the integrity proofs to the blockchain. The second experiment is from the perspective of those who want to audit the transactions (i.e., verify transaction integrity) and involves querying the transaction layer for a data sharing transaction event, recomputing the event's integrity proof, querying the blockchain for the integrity proof and verifying the integrity. The elapsed execution time of both experiments is plotted in FIG. 9. Each reported elapsed time is the average of three independent executions. It can be seen that the graphs validate the linear time growth of both perspectives.

In our experiments, we observed a linear scaling of time cost with respect to the growing number of transactions. Note that the transactions in the experiment were performed sequentially, and represent a worst-case upper bound for the transaction scaling. In a real world use case, transactions are performed by distributed users (e.g., researchers) across multiple nodes. In such a scenario, the transaction processing can be done concurrently since different transactions can be invoked and completed independently. The concurrent processing of transactions will result in lowering the transaction scaling complexity of the overall system.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

[1] The Economist, "Apple and amazon's moves in health signal a coming transformation," February 2018. [Online]. Available: https://www.economist.com/news/business/21736193-worlds-biggest-tech-firms-see-opportunity-health-care-which-could-mean-empowered

[2] M. Mercuri, M. M. Rehani, and A. J. Einstein, "Tracking patient radiation exposure: Challenges to integrating nuclear medicine with other modalities," *Journal of Nuclear Cardiology*, vol. 19, no. 5, pp. 895-900, 2012. [Online]. Available: http://dx.doi.org/10.1007/s12350-012-9586-x

[3] M. M. Rehani, "Challenges in radiation protection of patients for the 21st century," *American Journal of Roentgenology*, vol. 200, no. 4, pp. 762-764, 2013.

[4] R. Samavi and M. P. Consens, "Publishing l2tap logs to facilitate transparency and accountability," in The 23$^{rd}$ *International World Wide Web Conference (WWW'14) Workshop on Linked Data on the Web*, 2014.

[5] M. J. Field, B. Lo et al., *Conflict of interest in medical research, education, and practice*. National Academies Press, 2009.

[6] B. Schneier, *Applied cryptography: protocols, algorithms, and source code in C*. john wiley & sons, 2007.

[7] P. Alexander, G. Kimmell, and D. Burke, "Security as a system property: Modeling trust and security in rosetta," 2007.

[8] Symantec, 2018. [Online]. Available: https://www.symantec.com/

[9] MIT Kerberos, "Kerberos: The network authentication protocol," 2009. [Online]. Available: https://web.mit.edu/kerberos/

[10] Y. Li, "The case analysis of the scandal of enron," *International Journal of business and management*, vol. 5, no. 10, p. 37, 2010.

[11] C. A. Kushida, D. A. Nichols, R. Jadrnicek, R. Miller, J. K. Walsh, and K. Griffin, "Strategies for de-identification and anonymization of electronic health record data for use in multicenter research studies," *Medical care*, pp. S82-S101, 2012.

[12] G. S. Nelson, "Practical implications of sharing data: a primer on data privacy, anonymization, and de-identification," in *SAS Global Forum Proceedings*, 2015.

[13] F. Zafar, A. Khan, S. Suhail, I. Ahmed, K. Hameed, H. M. Khan, F. Jabeen, and A. Anjum, "Trustworthy data: A survey, taxonomy and future trends of secure provenance schemes," *Journal of Network and Computer Applications*, vol. 94, pp. 50-68, 2017.

[14] J. Freire, D. Koop, E. Santos, and C. T. Silva, "Provenance for computational tasks: A survey," *Computing in Science & Engineering*, vol. 10, no. 3, 2008.

[15] H. K. Patil and R. Seshadri, "Big data security and privacy issues in healthcare," in *Big Data (BigData Congress), 2014 IEEE International Congress on*. IEEE, 2014, pp. 762-765.

[16] K. Veeramachaneni, I. Arnaldo, A. Cuesta-Infante, V. Korrapati, C. sBassias, and K. Li, "Ai$^2$: Training a big data machine to defend," in *IEEE International Conference on Intelligent Data and Security (IDS'16)*, April 2016, pp. 49-54.

[17] HL7 International, "Fhir," 2017, accessed June 2017. [Online]. Available: https://www.hl7.org/fhir/index.html

[18] T. Heath and C. Bizer, "Linked data: Evolving the web into a global data space," *Synthesis lectures on the semantic web: theory and technology*, vol. 1, no. 1, pp. 1-136, 2011.

[19] J. J. Carroll, C. Bizer, P. Hayes, and P. Stickler, "Named graphs, provenance and trust," in *Proceedings of the 14th international conference on World Wide Web*. ACM, 2005, pp. 613-622.

[20] R. Samavi and M. P. Consens, "Publishing privacy logs to facilitate transparency and accountability," in *The Journal of Web Semantics*, 2018.

[21] A. Sutton and R. Samavi, "Blockchain enabled privacy audit logs," in *Proceedings of the 16th International Semantic Web Conference*. Springer, 2017, pp. 1-16.

[22] A. Sambra, H. Story, and T. Berners-Lee, "Webid 1.0: Web identity and discovery," March 2014. [Online]. Available: https://www.w3.org/2005/Incubator/webid/spec/identity/

[23] M. Mettler, "Blockchain technology in healthcare: The revolution starts here," in *IEEE 18$^{th}$ International Conference on e-Health Networking, Applications and Services (Healthcom'16)*, September 2016, pp. 1-3.

[24] A. Azaria, A. Ekblaw, T. Vieira, and A. Lippman, "Medrec: Using blockchain for medical data access and permission management," in *2nd International Conference on Open and Big Data (OBD'16)*, August 2016, pp. 25-30.

[25] X. Yue, H. Wang, D. Jin, M. Li, and W. Jiang, "Healthcare data gateways: Found healthcare intelligence on blockchain with novel privacy risk control," *Journal of Medical Systems*, vol. 40, no. 10, p. 218, 2016. [Online]. Available: http://dx.doi.org/10.1007/s10916-016-0574-6

[26] K. Peterson, R. Deeduvanu, P. Kanjamala, and K. Boles, "A blockchain-based approach to health information exchange networks," 2016.

[27] M. Pilkington, "Blockchain technology: principles and applications," *Research Handbook on Digital Transformations*, 2015.

[28] S. Nakamoto, "Bitcoin: A peer-to-peer electronic cash system," 2008.

[29] S. Melnik, "Rdf api draft: Cryptographic digests of rdf models and statements," 2001. [Online]. Available: http://www-db.stanford.edu/~melnik/rdf/api.html#diges

[30] J. J. Carroll, "Signing rdf graphs," in *International Semantic Web Conference*. Springer, 2003, pp. 369-384.

[31] C. Sayers and A. H. Karp, "Computing the digest of an rdf graph," *Mobile and Media Systems Laboratory, HP Laboratories, Palo Alto, USA, Tech. Rep. HPL*-2003-235, vol. 1, 2004.

[32] J. A. Fisteus, N. F. Garcia, L. S. Fernandez, and C. D. Kloos, "Hashing and canonicalizing notation 3 graphs," *Journal of Computer and System Sciences*, vol. 76, no. 7, pp. 663-685, 2010.

[33] A. Sutton and R. Samavi, "Timestamp-based integrity proofs for linked data," in *Proceedings of the International Workshop on Semantic Big Data*. ACM, 2018, p. 4.

[34] C. Castelluccia, P. Druschel, S. Hubner, A. Pasic, B. Preneel, and H. Tschofenig, "Privacy, accountability and trust-challenges and opportunities," *ENISA*. [*Online*]. Available: http://www.enisa.europa.eu/activities/identity-and-trust/library/deliverables/pat-study/at download/fullReport, 2011.

[35] HL7 International, "Fhir security," 2017, accessed April 2018. [Online]. Available: https://www.hl7.org/fhir/security.html

[36] D. Bradbury, "The problem with bitcoin," *Computer Fraud & Security*, vol. 2013, no. 11, pp. 5-8, 2013.

[37] Microsoft, "The stride threat model," 2005. [Online]. Available: https://msdn.microsoft.com/en-us/library/ee823878(v=cs.20).aspx

[38] OpenLink Software, "Virtuoso universal server," 2017. [Online]. Available: https://virtuoso.openlinksw.com/

[39] The Linux Foundation, "Hyperledger fabric documentation," 2018, accessed June 2017. [Online]. Available: https://hyperledger-fabric.readthedocs.io/en/release-1.1/

[40]—, "Hyperledger explorer," 2018. [Online]. Available: https://www.hyperledger.org/projects/explorer

[41] L. A. Linn and M. B. Koo, "Blockchain for health data and its potential use in health it and health care related research," 2017.

[42] C. McFarlane, M. Beer, J. Brown, and N. Prendergast, "Patientory: A healthcare peer-to-peer emr storage network v1.0," 2017.

[43] J. Sotos and D. Houlding, "Blockchains for data sharing in clinical research: Trust in a trustless world," 2017.

[44] X. Liang, J. Zhao, S. Shetty, J. Liu, and D. Li, "Integrating blockchain for data sharing and collaboration in mobile healthcare applications," in *Personal, Indoor, and Mobile Radio Communications (PIMRC), 2017 IEEE 28th Annual International Symposium on*. IEEE, 2017, pp. 1-5.

[45] G. Zyskind, O. Nathan, and A. Pentland, "Decentralizing privacy: Using blockchain to protect personal data," in 2015 *IEEE Security and Privacy Workshops*, May 2015, pp. 180-184.

[46] L. Xu, L. Chen, N. Shah, Z. Gao, Y. Lu, and W. Shi, "Dl-bac: Distributed ledger based access control for web applications," in *Proceedings of the 26th International Conference on World Wide Web Companion*. International World Wide Web Conferences Steering Committee, 2017, pp. 1445-1450.

[47] M. Suleyman and B. Laurie, "Trust, confidence and verifiable data audit," March 2017. [Online]. Available: https://deepmind.com/blog/trust-confidence-verifiable-data-audit/

[48] Google, "Trillian," https://github.com/google/trillian, 2018.

[49] A. Eijdenberg, B. Laurie, and A. Cutter, "Verifiable data structures," November 2015. [Online]. Available: https://github.com/google/trillian/blob/master/docsNerifiable-DataStructures.pdf

APPENDIX 1

III. Privacy, Security & Trust

In this section, we discuss how our architecture addresses important privacy and security properties in the health research domain. We then summarize the trustworthiness of the architecture in terms of our defined trust requirements.

Accountability and Transparency. Information accountability is an important aspect of privacy protection and has three main characteristics: validation (verifies a posteriori if tasks were performed as expected), attribution (finding non-compliant participants), and evidence (supporting information of non-compliant acts) [21], [34]. In order to support account ability, our architecture captures privacy events in the transaction layer that records deontic modalities such as privacy policies, purpose of data usage, obligations, and data access activities as described in [20]. Although the privacy events do not provide enforcement of the participants' performed acts and does not guarantee the accuracy of the reported actions, the privacy events provide a mechanism to express actions that can be effectively audited. The transparent flow and exchange of information in health research is an important factor in determining the compliance of participants in the research environment. Our architecture supports transparency through the use of blockchain technology to allow all participants to query when, what, by whom and why data is being shared in the entire data lifecycle. The transparency layer supports the concept of human-in-the-loop by allowing all participants to actively audit the sharing of private health data.

Confidentiality and Integrity. The confidentiality of private health data is achieved through the use of encryption. Since our architecture relies on the sharing of data pointers, the actual data records do not leave their secure storage in data repositories at hospitals and research institutes. The data accessible through the pointers are encrypted at rest in the repositories. For example, the data repositories leverage a public key infrastructure (PKI) to encrypt the data with the data sharing recipient's public key, where only the recipient can decrypt the data using their private key. The integrity of the data sharing transactions is guaranteed by the integrity proofs that are stored on the blockchain in the transparency layer. Since the blockchain provides a tamper-proof storage mechanism for the integrity proofs, the integrity proofs in the blockchain can reliably be used for data sharing transaction integrity verification purposes.

Authentication and Access Control. To support authentication, the transparency layer utilizes a permissioned blockchain network that allows only authenticated participants (e.g. patients, researchers, hospitals) whose identity is verified through a PKI to transact and query the blockchain. A PKI allows our network to leverage a multi-signature consensus mechanism where n-out-of-m (where n<m and n>1) signatures are required to validate transactions. Unlike proof-of-work consensus mechanisms [28] that are employed in public blockchain networks, a signature consensus only requires a majority of participant signatures to determine valid transactions and write data to the blockchain. Our architecture employs access control mechanisms to prevent unauthorized users from accessing private health data. Specifically, the access decision for participants who can perform data sharing transactions (e.g., write transactions to the transaction layer's endpoint or generate a data pointer in the data layer) is determined at the respective layers through mechanisms such as keys, certificates, tokens, passwords, and institutional access control mechanisms. Data sharing transaction types are limited to specific users, for example, $T_{outcome}$ transactions are only performed by AI systems and only authorized users, such as researchers, can view the results, whereas $T_{pointer}$ transactions

TABLE II

System Trustworthiness Summary

| Architectural Component | Conf. | Integrity | Auth. | Non-rep. | Acc. | Avail. |
|---|---|---|---|---|---|---|
| Transparency Layer | ✓ | ✓ | ✓ | ✓ | ✓ | Out of Scope |
| Transaction Layer | ✓ | — | ✓ | ✓ | ✓ | Out of Scope |
| Data Layer | ✓ | — | ✓ | — | — | Out of Scope | can be performed by any user (e.g., researcher or AI system). Since each network participant can be identified through digital signatures, participant authentication and transactions can be verified.

Trustworthiness. To determine the trustworthiness of our proposed system, we must examine how each of the architectural components addresses the six trust requirements outlined in Section II-A. Our proposed architecture is composed of three modular layers, the transparency, transaction, and data layers, so we examine each of the layers in terms of each trust property.

The transparency layer's key feature is the use of a permissioned blockchain, which means this layer must support all six properties. In terms of confidentiality and integrity, the blockchain supports encrypted data over the network and provides an immutable digital ledger of transactions. A permissioned blockchain network supports authentication and access control through network entity identification (i.e., digital signatures, certificates). All transactions on the network are digitally signed to achieve non-repudiation. A blockchain supports the transparency and accountability of participants on the network since all data interactions are stored on the blockchain and all transactions are verified through a consensus protocol. Furthermore, all data transformations and interactions across the research pipeline can be audited by the blockchain network participants.

The transaction layer operates as a data query endpoint, which provides confidentiality through data at rest encryption services. Only authenticated and authorized users can interact with the transaction layer to store data relating to data sharing events. Non-repudiation is achieved since all data sharing events stored in the transaction layer are digitally signed by the event generator. All data sharing events capture the provenance and privacy information relating to each individual data sharing event to capture the accountability of all actors participating in the sharing of data. Data sharing event integrity is not directly supported in this layer, rather the integrity proof of the transaction is preserved in the transparency layer.

The data layer offers data pointer generation services and provides the secure storage for the actual data records. By leveraging data pointers, we support the access control mechanisms enforced at local hospitals where the actual data records reside. Furthermore, the FHIR data pointer framework supports the authentication of users and provides role-based (RBAC) and attribute-based (ABAC) access control mechanisms [35]. The data pointer repositories also support confidentiality by providing encryption services to protect the data at rest. Similar to the transaction layer, the data layer does not directly achieve integrity, non-repudiation, and accountability, rather these properties are indirectly captured in the transparency and transaction layers.

Table II provides a summary of the system trustworthiness in terms of the six requirements for establishing trust. Although we achieve many of the requirements for establishing trust, there are some limitations with respect to the trust properties. We discuss these limitations in the adversarial threat characterization of Section IV-A.

IV. Evaluation

In this section, we first enumerate an adversary's capabilities when interacting with our architecture (Section IV-A). Then, we investigate our system's resiliency to common security threats using an industry standard threat model (Section IV-B). We then experimentally evaluate the realization of our architecture in Section IV-C.

A. Adversarial Threat Characterization

We classify the goals of an adversary as compromising the confidentiality or integrity of the private health data. An adversary compromises the confidentiality of the data by having unauthorized access to and reading plaintext data, whereas an integrity compromise refers to the malicious and unintended manipulation of the data. In terms of data confidentiality, our architecture relies solely on the sharing of data pointers rather than the actual private data records. Since we leverage FHIR as our data pointers, we rely on the institutional access control mechanisms to manage users' access rights when using the pointer to read the data. The data behind the pointer is encrypted at the data source. Although, the data pointer itself is not encrypted for auditing purposes, we can apply obfuscating techniques to the pointer so that no potentially private information is leaked through the URL. Since we utilize an immutable ledger in the form of a blockchain, all transactions have immutable integrity proofs stored in the blockchain. Attempts made by the adversary to perform retrospective modification of any transaction records will fail the integrity verification process in the transparency layer.

Based on the design of our proposed architecture, in a worst-case scenario, we assume that an adversary has three attack surfaces to potentially exploit: the transparency, transaction, and data layers. Since a blockchain serves as our transparency layer, the adversary would have to successfully become a participant in the blockchain network to potentially exploit attacks. However, we leverage a private (permissioned) blockchain network where participants' identities are known and participants are granted certificates for digital signatures through a certificate authority. Therefore, a more likely attack vector is from an insider adversary, where they have successfully enrolled in the network. In fact, in this case, the consensus mechanism leveraged by the network can prevent an adversarial participant in the network from exhibiting malicious behaviour since all transactions must be verified and accepted by network participants. Majority-based consensus protocols give rise to a majority attack on the network, where 51% of the network must be adversarial to overcome the benign nodes, but these majority attacks are more common in public blockchain settings rather than private settings (due to the different consensus protocols used) [36].

At the transaction layer, although the confidentiality and authenticity of the transactions are supported, an internal attacker has the opportunity to generate and inject fake data sharing events (e.g., to possibly to hide non-compliant actions) into the system to subvert the verification process. Since collaborating participants perform data sharing transactions with each other, an internal attacker could create events that do not represent the true data transformation or activity that occurred (e.g., an adversary could create a fake and misleading privacy event). However, through retrospective auditing and the fact that all network participants are known, the adversary will be caught and identified by their digital signature (assuming the signing key was not stolen or the adversary is not masquerading as another entity). Furthermore, to be successful, an attacker would have to generate and sign a fake data sharing transaction, store the events in the transaction layer, calculate an integrity proof, and have the integrity proof transaction successfully verified and accepted by participants on the blockchain.

The data layer relies on the institutional-based protection mechanisms for preventing adversarial threats. Since the data layer stores the actual data records, it makes a prime target for an adversary to access private patient data. For this reason, we only interact and store pointers to this data in subsequent architectural layers so that hospitals and research institutes (i.e., data custodians) remain in operational control of their data and can apply their security policies to provide the safe and secure storage of data.

B. Threat Model Assessment

We assess our architecture using the Spoofing, Tampering, Repudiation, Information disclosure, Denial of Service, Elevation of privilege (STRIDE) threat classification methodology developed by Microsoft [37].

Spoofing. Since we leverage secure PKI, users cannot masquerade as another user (unless their private key has been exposed).

Tampering. Since we leverage a blockchain, the integrity proof stored in the blockchain cannot be altered. A data sharing transaction that is tampered with in the transaction layer can be detected by verifying the integrity of the transaction since there is an immutable integrity proof of the transaction stored in the blockchain.

Repudiation. All data sharing transactions are digitally signed by the initiator of the transaction, so users cannot deny the actions they have taken (assuming signing keys are not compromised).

Information disclosure. Since our architecture relies on sharing data pointers rather than actual data records, the likelyhood of a data record privacy breach is reduced. In the case of data leakage to unauthorized parties, the URL used to access the data can be terminated so that the data cannot be accessed through that URL. Access to the data at the URL is governed by secure access control mechanisms at the data source (password protection, one-time password generation, data is encrypted, etc.).

Denial of Service (DoS) and Elevation of privilege. These types of threats are out of the scope of our architecture and we rely on external mechanisms to address these threats.

The invention claimed is:

1. A system to enable verifiable trust in collaborative data-sharing environments, comprising,
   a data layer, storing primary data of interest and generating a data pointer that links to the primary data of interest;
   a transaction layer, storing a data sharing transaction, the data sharing transaction including the data pointer and a privacy policy associated with the primary data of interest; and
   a transparency layer, storing a chain of verifiable integrity checks for verifying the integrity of each layer.

2. The system of claim 1, wherein a permissioned blockchain is used as a plug-in for the transparency layer.

3. The system of claim 1, wherein the data layer includes a data repository hosted at a hospital or research institute.

4. The system of claim 1, wherein the data sharing transaction further includes a signing event.

5. The system of claim 4, wherein the signing event includes a digital signature.

6. A method to enable verifiable trust in collaborative data sharing environments, comprising:
   storing data in a data layer;
   generating a data pointer that links to the data in the data layer;
   constructing a data sharing transaction, the data sharing transaction including the data pointer;
   storing the data sharing transaction in a transaction layer separate from the data layer, the transaction layer available so that a third party can review the data sharing transaction and access the data pointer;
   computing an integrity proof of the data sharing transaction; and
   writing the integrity proof to a transparency layer accessible by the third party.

7. The method of claim 6, wherein storing the data in the data layer includes storing the data in a data repository of the data layer which is hosted at a hospital or research institute.

8. The method of claim 6, wherein the data sharing transaction includes a privacy event and a signing event.

9. The method of claim 8, wherein the privacy event captures promised and performed privacy acts.

10. The method of claim 9, wherein the promised and performed privacy acts include expressing privacy policies and defining data usage obligations.

11. The method of claim 8, wherein the signing event captures a digital signature of a data sender.

12. The method of claim 6, wherein the system supports at least two types of sharing transactions, the at least two types of sharing transactions including:
   a pointer transaction type sharing at least one pointer referencing patient data in the data layer; and
   an outcome transaction type sharing an outcome generated by an artificial intelligence system, and wherein constructing the data sharing transaction includes specifying that the data sharing transaction is either the pointer transaction type or the outcome transaction type.

13. A method to enable verifiable trust in collaborative data sharing environments, comprising:
    querying a transparency layer of a collaborative system;
    verifying the integrity of a data sharing transaction of a transaction layer of the collaborative system by recomputing an integrity proof of the data sharing transaction and comparing the integrity proof to the transparency layer;
    querying the transaction layer to determine a privacy policy to abide by when using data available via a data pointer specified in the data sharing transaction; and
    accessing the data at a data layer of the collaborative system through the data pointer specified in the data sharing transaction.

14. The method of claim 13, wherein accessing the data at the data layer includes accessing the data in a data repository of the data layer which is hosted at a hospital or research institute.

* * * * *